United States Patent [19]

Issei

[11] 4,276,125

[45] Jun. 30, 1981

[54] PROCESS FOR PURIFICATION OF CRUDE OLEFINICALLY UNSATURATED NITRILE AND CONDENSER USEFUL FOR SAME PROCESS

[75] Inventor: Katsuta Issei, Kurashiki, Japan

[73] Assignee: Asahi Kasei Kogyo Kabushiki Kaisha, Osaka, Japan

[21] Appl. No.: 115,594

[22] Filed: Jan. 25, 1980

[30] Foreign Application Priority Data

Feb. 2, 1979 [JP] Japan .................................. 54-11110
Feb. 2, 1979 [JP] Japan .................................. 54-11112

[51] Int. Cl.$^3$ ............................................. B01D 3/00
[52] U.S. Cl. ........................................ 203/4; 203/98; 203/DIG. 3; 203/DIG. 19
[58] Field of Search .............. 203/91, 94, 98, DIG. 3, 203/DIG. 19, 4; 260/465.3, 465.9

[56] References Cited

U.S. PATENT DOCUMENTS

| | | | |
|---|---|---|---|
| 3,080,301 | 3/1963 | Fontana et al. | 203/97 |
| 3,149,055 | 9/1964 | Hougland | 203/98 |
| 3,696,003 | 10/1972 | Fitch et al. | 203/4 |

OTHER PUBLICATIONS

"Chemical Engineer's Handbook"; Perry; 4th Ed., pp. 11-2, 11-3 & 11-8.

*Primary Examiner*—Frank Sever

*Attorney, Agent, or Firm*—Sprung, Felfe, Horn, Lynch & Kramer

[57] ABSTRACT

A process for purifying a crude olefinically unsaturated nitrile containing hydrogen cyanide and water by feeding the crude olefinically unsaturated nitrile at a point above the middle of a rectifying column for stripping hydrogen cyanide, withdrawing and condensing a vapor of hydrogen cyanide from the top of the column while withdrawing the olefinically unsaturated nitrile and water from the bottom of the column, which process comprises withdrawing a vapor in the column at a point between the top of the column and the point of introduction of the crude olefinically unsaturated nitrile at a substantially constant rate, cooling and condensing the vapor withdrawn in a condenser having an outlet for non-condensing gas while continuously withdrawing non-condensing gas in the vapor from the condenser, and returning the condensate liquid to the column at an intermediate point between the point of introduction of the crude olefinically unsaturated nitrile and the top of the column, and a condenser useful for the above described process which comprises an heat exchange section having an inlet for vapor at its upper part and a liquid reservoir section having an outlet for condensate liquid at its lower part and an opening at the side wall of the liquid reservoir section, the opening being connected with a conduit for withdrawing non-condensing gas from the condenser.

11 Claims, 3 Drawing Figures

PROCESS FOR PURIFICATION OF CRUDE OLEFINICALLY UNSATURATED NITRILE AND CONDENSER USEFUL FOR SAME PROCESS

BACKGROUND OF THE INVENTION

1. Field of the Invention

This invention relates to a process for purifying a crude olefinically unsaturated nitrile such as acrylonitrile and methacrylonitrile containing hydrogen cyanide and water by removal of the hydrogen cyanide. Also, it relates to a condenser useful for the same process.

2. Description of the Prior Art

In the conventional process, the reaction gas obtained in the ammoxidation of propylene or isobutylene is fed to a quenching column where unreacted ammonia is removed. Then the reaction gas quenched is countercurrently contacted with absorbing water in an absorption column, and a reaction exhaust gas containing unreacted propylene or unreacted isobutylene, carbon monoxide, carbon dioxide, nitrogen etc. is dicharged from the top of the absorption column while an aqueous solution mainly containing acrylonitrile or methacrylonitrile, acetonitrile and hydrogen cyanide is withdrawn from the bottom of the absorption column. The aqueous solution thus obtained is fed to an extractive distillation column, to the upper part of which water is introduced as an extractant. The distillate from the top of the extractive distillation column is condensed and an acrylonitrile or methacrylonitrile solution containing hydrogen cyanide and water is recovered. Then the acrylonitrile or methacrylonitrile solution after removal of non-condensing gas is fed to a rectifying column and from the top of the rectifying column is recovered hydrogen cyanide while from the bottom of the rectifying column is recovered acrylonitrile or methacrylonitrile and water.

The concentration of hydrogen cyanide in the vapor obtained from the top of the rectifying column is high and the cooling temperature of a condenser must be maintained lower than the boiling point of hydrogen cyanide. For this reason, cooling water from a cooling tower which is usually employed is not suitable as the cooling medium, and accordingly, water refrigerated with a cooling medium such as ammonia or freon has been used, resulting in an increase in power consumption.

According to another process for conducting the rectification at a high efficiency as described in U.S. Pat. No. 3,507,755, a crude acrylonitrile is fed into a distillation column at a point just above the middle of the column and the liquid within the column is withdrawn just below the point of introduction of the crude acrylonitrile, cooled and separated into two phases, i.e. an upper organic phase rich in acrylonitrile and a lower aqueous phase rich in water. The lower aqueous phase is withdrawn while the upper organic phase is returned to the column at a point just below the point of withdrawal of the liquid. In this process, by-produced impurities such as acetone, acrolein and acrolein cyanohydrin which are contained in the lower aqueous phase can be removed together with water, and as a result, from the bottom of the column is obtained an acrylonitrile solution having a much more improved purity than that obtained by the conventionally employed process while from the top of the column is obtained hydrogen cyanide having a higher purity. Further, a comparative reduction in consumption of steam for heating the column can be achieved. However, in this rectifying process, the concentration of hydrogen cyanide in the vapor from the top of the column reaches at least about 96% by weight and the temperature of the top of the column becomes about 30° C. due to the boiling point of hydrogen cyanide of 25.7° C. and accordingly, refrigerated water having a low temperature is also required as the cooling medium for the condenser in an atmospheric pressure operation, resulting in a marked increase in cost of power and equipment for the refrigerator for cooling. In order to condense the vapor having such a temperature with ordinary cooling water, an extremely large area of heat transmission for cooling is required due to the small difference of temperature between the vapor and the cooling water. As a result, the industrial feasibility of this process is small in spite of its advantages. On the other hand, it may be considered that operation of the column under a higher pressure renders cooling for condensation easier due to increased temperatures of the top of the column, but the temperature of the bottom of the column is simultaneously increased. As a result, polymerization of acrylonitrile in the liquid of the column is disadvantageously increased for practical purposes.

In general, when a vapor containing non-condensing gas is condensed, its condensation is conducted while withdrawing the non-condensing gas from an outlet of the condensation system provided at a suitable point. Such a point is usually the top of a condenser. However, when the condensation is conducted by a condenser having an outlet at its top, at least two series of control systems, one for the level of the condensate liquid and the other for the amount of the vapor fed to the condenser or the amount of the condensate liquid withdrawn, are required for controlling the amount of condensation or the condensation of vapor at a constant flow rate. Several methods are employed for this purpose. For example, the amount of the vapor fed is controlled at a constant flow rate and the amount of condensation is controlled in such a manner that the level of the condensate liquid is kept constant. Or the flow amount of cooling water in the condenser is controlled in order to maintain the amount of vapor constant, and the flow amount of the condensate liquid is controlled in such a manner that the level of the condensate liquid is kept constant. In the above described methods, any regard is not given to the control of withdrawing non-condensing gas.

SUMMARY OF THE INVENTION

An object os this invention is, therefore, to provide a process for purifying a crude olefically unsaturated nitrile containing hydrogen cyanide and water which can remarkably reduce the cooling load for a condenser at the top of a rectifying column for stripping hydrogen cyanide by refrigerated water and which can replace the refrigerated water with cooling water of a higher temperature such as cooling water from a cooling tower in achieving the same rectifying result as with refrigerated water.

Another object of this invention is to provide a condenser for vapor useful for the same process.

Still another object of this invention is to provide a process for regulating the amount of condensation using the same condenser.

Accordingly, there is provided a process for a crude olefinically unsaturated nitrile containing hydrogen cyanide and water by feeding the crude olefinically unsaturated nitrile at a point above the middle of a rectifying column for stripping hydrogen cyanide, withdrawing and condensing a vapor of hydrogen cyanide from the top of the column while continuously withdrawing the olefinicallt unsaturated nitrile and water from the bottom of the column, which process comprises withdrawing a vapor in the column at a point between the top of the column and the point of introduction of the crude olefinically unsaturated nitrile at a substantially constant rate, cooling and condensing the vapor withdrawn in a condenser having an outlet for non-condensing gas while continuously withdrawing the non-condensing gas in the vapor from the condenser, and returning the condensate liquid to the column at an intermediate point between the point of introduction of the crude olefinically unsaturated nitrile and the top of the column.

According to another embodiment of this invention, there is provided a condenser comprising an heat exchange section having an inlet for vapor at its upper part and a liquid reservoir section having an outlet for condensate liquid at its lower part and an opening at the side wall of the liquid reservoir section, the opening being connected with a conduit for withdrawing non-condensing gas from the condenser.

According to still another embodiment of this invention, there is provided a process for continuously condensing a vapor containing non-condensing gas by the same condenser as described above which comprises feeding the vapor to the inlet for vapor, varying the level of the condensate liquid in the liquid reservoir section by regulating the flow amount of the condensate liquid withdrawn from the outlet for condensate liquid and regulating the pressure within the condenser by varying the area of the opening for withdrawing non-condensing gas, whereby the amount of condensation is regulated.

DETAILED DESCRIPTION OF THE INVENTION

Figure 1:
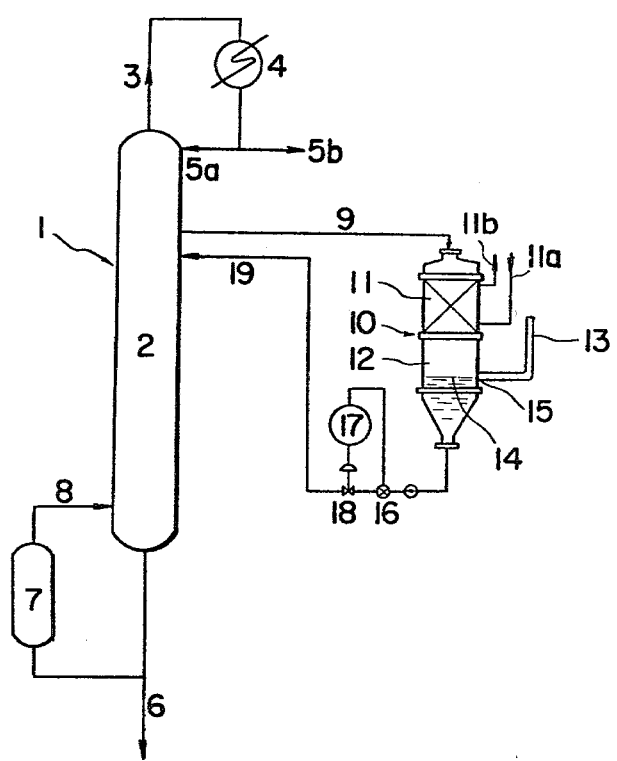
FIG. 1 shows a flow diagram of a typical embodiment of the process of this invention.

The crude olefinically unsaturated nitriles containing hydrogen cyanide and water which can be employed in this invention include a crude acrylonitrile and a crude methacrylonitrile. This invention will be explained in greater detail with a crude acrylonitrile as the crude olefinically unsaturated nitrile.

The crude acrylonitrile which is typically employed in this process is the one obtained from the top of an extractive distillation column and degassed and typically contains about 60 to about 90% by weight of acrylonitrile, about 5 to about 15% by weight of hydrogen cyanide, about 3 to about 10% by weight of water and a small amount of carbonyl compounds.

The rectifying column for stripping hydrogen cyanide which can be employed for purifying such a crude acrylonitrile in this invention typically has at least about 20 plates and preferably about 30 plates to about 50 plates. The rectifying column for stripping hydrogen cyanide and dehydration which can also be employed in this invention typically has at least about 30 plates and preferably about 35 plates to about 70 plates. As the distillation column, the rectifying column for stripping hydrogen cyanide and dehydration is preferred since another dehydration column is unnecessary and the consumption of steam is smaller.

The crude acrylonitrile as a feed is supplied to the rectifying column at a point above the middle of the column. According to this invention, the withdrawal of a vapor within the column is conducted at an intermediate point between the point of introduction of the crude acrylonitrile and the top of the column, i.e. a enriching section of the column with hardly any affect on the composition of the bottoms liquid. On the other hand, when the withdrawal of the vapor is conducted at an intermediate point between the point of introduction of the crude acrylonitrile and the bottom of the column, i.e. a recovery section of the column, the concentration of hydrogen cyanide in the acrylonitrile and water obtained from the bottom of the column is disadvantageously increased. In some cases, an increase in the amount of acrylonitrile in the hydrogen cyanide obtained from the top of the column can be observed in the withdrawal of the vapor of this invention. This increase, however, can be prevented by appropriately selecting the point where the withdrawal of the vapor is conducted and the amount of the vapor withdrawn. When the point of withdrawal of the vapor becomes nearer to the point of introduction of the crude acrylonitrile, the area for heat transmission in the condenser for the vapor withdrawn is decreased due to the increase in the difference of temperature between the vapor and the cooling water in the condenser but the section of a small reflux ratio in the column, i.e. the section between the top of the column and the point of withdrawal of the vapor becomes larger and accordingly, hydrogen cyanide is not enriched, resulting in an increase in the amount of acrylonitrile in the hydrogen cyanide obtained from the top of the column. On the other hand, when the point of withdrawal of the vapor becomes nearer to the top of the column, the section of a small reflux ratio in the column becomes smaller and hardly any increase in the amount of acrylonitrile in the hydrogen cyanide obtained from the top of the column can be observed. However, the area for heat transmission in the condenser for the vapor withdrawn is enormously increased due to the small difference in temperature between the vapor and cooling water and it becomes impossible to condense the vapor with ordinary cooling water. Thus, it is preferred that the withdrawal of the vapor is conducted at an intermediate point where the temperature in the column is about 40° C. to about 75° C. between the top of the column and the point of introduction of the crude acrylonitrile. A more preferred point of withdrawal of the vapor has a temperature of about 55° C. to about 70° C. in the column. More specifically, the withdrawal of the vapor is conducted at a plate between about the second plate and about the 20th plate from the top of the column and preferably between about the 5th plate and about the 15th plate from the top of the column.

The amount of the vapor withdrawn which can be employed in this invention is typically at least 10% by weight of the total amount of the ascending vapor in the column and preferably ranges from about 50 to about 90% by weight of the total amount of the ascending vapor in the column. When the amount of the vapor withdrawn is more than about 90% by weight, the reflux ratio at the section between the top of the column and the point of withdrawal of the vapor is decreased and the amount of acrylonitrile in hydrogen cyanide obtained from the top of the column tends to be increased. On the other hand, when the amount of the vapor withdrawn is less than about 10% by weight, the heat load of the condenser provided at the top of the column cannot be reduced.

The vapor withdrawn is cooled and condensed in a condenser while continuously withdrawing non-condensing gas in the vapor from the condenser. The condensate liquid can be returned to the column at an intermediate point between the point of introduction of the crude acrylonitrile and the top of the column. When the condensate liquid is returned to the column at the top of the column, the amount of acrylonitrile in the hydrogen cyanide at the top of the column is increased. On the other hand, when the condensate liquid is returned to the column at a point nearer to the bottom of the column, the amount of hydrogen cyanide in the acrylonitrile is increased. In the process of this invention, it is preferred that the condensate liquid is returned at a point where the temperature in the column is about 40° C. to about 75° C. More specifically, the condensate liquid is preferably returned to the second plate to about the 20th plate from the top of the column. A more preferred point were the condensate liquid is returned is just below the point of withdrawal of the vapor, i.e. one plate below the plate of withdrawal of the vapor or the same point of withdrawal of the vapor, i.e. the same plate as the plate of withdrawal of the vapor.

According to this invention, the continuous withdrawal of the non-condensing gas including carbon dioxide is essential. When the vapor withdrawn is cooled and condensed with orginary cooling water whose temperature is about 20° C. to 30° C. in a condenser without withdrawing the non-condensing gas from the condenser, the vapor does not come into the condenser with the passage of several minutes after the start of the operation of the condenser and its condensation becomes impossible.

Any condensers for cooling and condensing the vapor withdrawn can be employed in this invention and it is preferred that the condenser is of a vertical type from the viewpoint of avoiding clogging due to the polymerization of hydrogen cyanide adhered to the wall of the condenser. A more preferred condenser which can be employed in this invention will be explained with reference to FIGS. 1 and 2.

When the rectifying column for stripping hydrogen cyanide and dehydration, i.e. a single column having the function of a column for stripping hydrogen cyanide and that of a column for dehydration is employed, in addition to the above described procedures, substantially all of the liquid descending in the column is withdrawn from the column at an intermediate point between the point of introduction of the crude olefinically unsaturated nitrile and the bottom of the column, cooled and separated into an organic phase and an aqueous phase in a decanter, and then the organic phase is returned to the column at a point below the intermediate point while withdrawing the aqueous phase from the decanter.

According to the present invention, a part or the greater part of refrigerated water which is employed in the overhead condenser can be replaced with ordinary cooling water having a temperature of about 20° C. to about 30° C. and as a result, the heat load of the overhead condenser can be reduced by at least about 65%.

This invention will now be explained in more detail with reference to the accompanying drawings.

FIG. 1 shows a flow diagram of a typical embodiment of the process of this invention.

In FIG. 1, numeral 2 denotes a rectifying column for stripping hydrogen cyanide; numeral 4 an overhead condenser; numeral 7 a reboiler; numeral 10 a condenser; numeral 11 the heat exchange section of condenser 10; numeral 12 the liquid reservoir section of condenser 10; numeral 13 a conduit for withdrawing non-condensing gas; numeral 14 a level of condensate liquid; numeral 15 an opening for withdrawing non-condensing gas; numeral 16 a liquid flow transmitter; numeral 17 a liquid flow controller; and numeral 18 a liquid flow control valve.

A crude olefinically unsaturated nitrile containing hydrogen cyanide and water is fed to the rectifying column for stripping hydrogen cyanide 2 through line 1 at a point above the middle of the column 2 and a vapor of hydrogen cyanide withdrawn from the top of the column 2 through line 3 is condensed in the overhead condenser 4, returned to the column 2 through line 5a and collected through line 5b. On the other hand, the olefinically unsaturated nitrile and water is withdrawn through line 6. The bottoms liquid in the column 2 is heated by steam at a reboiler 7 and circulated through line 8. A vapor in the column 2 is withdrawn at an intermediate point between the point of introduction of the crude olefinically unsaturated nitrile and the top of the column 2 and fed through line 9 to the condenser 19 and cooled and condensed in the heat exchange section 11 of the condenser 10 where a cooling medium such as industrial water and cooling water is introduced through line 11a and withdrawn through line 11b. If necessary, in order to prevent the polymerization of hydrogen cyanide, an inhibitor such as acetic acid may be fed in the condenser 10. The condensate liquid is collected in the liquid reservoir section 12 of the condenser 10 and withdrawn from the bottom of the liquid reservoir section 12 and returned to the column 2 through line 19. On the other hand, non-condensing gas is withdrawn from the condenser 10 at the opening 15 provided with the side wall of the liquid reservoir section 12 through a conduit 13. If necessary or if desired, a device for recovering hydrogen cyanide or acrylonitrile may be provided with the end of the conduit 13. Or the non-condensing gas may be returned to and withdrawn from the top of the extractive distillation column. The amount of condensation in the condenser 10 is regulated by a control system comprising a liquid flow transmitter 16, a liquid flow controller 17 and a liquid flow control valve 18. The method of regulating the amount of condensation will be explained with reference to FIG. 2.

Figure 2:
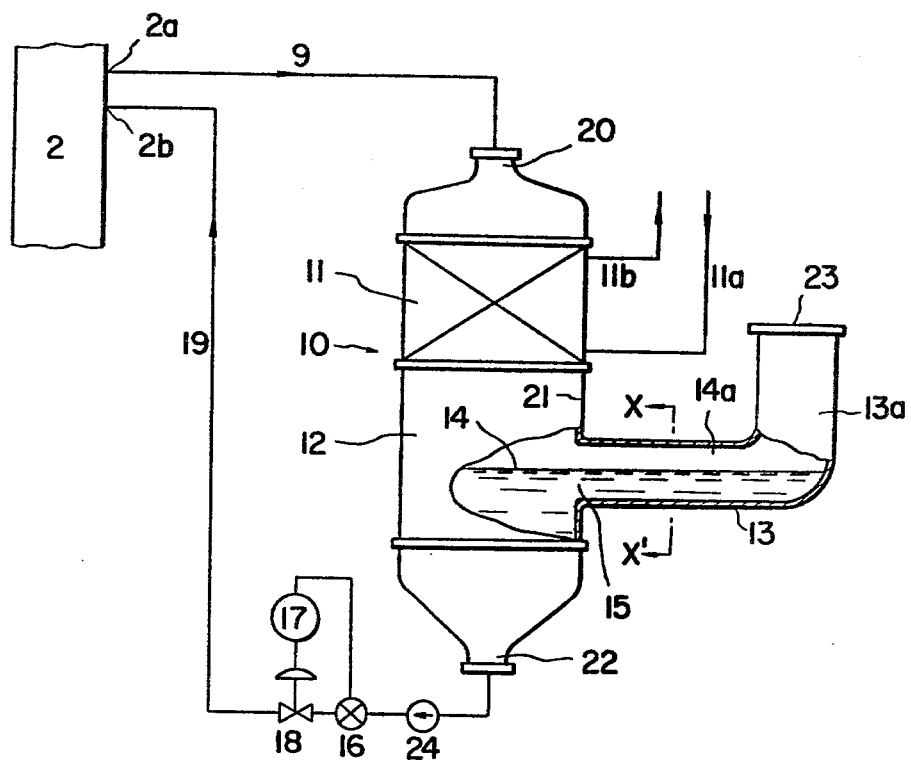
FIG. 2 shows a typical example of the condenser of this invention.

FIG. 2 shows a typical example of the condenser of this invention and a flow diagram of condensing a vapor containing non-condensing gas using the same condenser.

In FIG. 2, numeral 10 denotes a condenser which comprises a heat exchange section 11 and an inlet 20 for vapor at its upper part and a liquid reservoir section 12 for the condensate liquid at its lower part. At the side wall 21 of the liquid reservoir section 12 is provided an opening 15 which is connected with a conduit 13 for withdrawing non-condensing gas and the conduit 13 extends from the opening 15 to an outlet 23 for non-condensing gas at a higher position through its ascending section 13a. At the bottom of the liquid reservoir section 12 is provided an outlet 22 for withdrawing a condensate liquid. Numeral 14 denotes a level of the condensate liquid in the liquid reservoir section 4.

Figure 3:
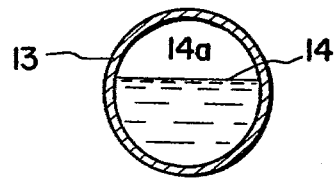
FIG. 3 shows a cross-sectional view of the level of the condensate liquid at the opening provided with the side wall of the liquid reservoir section in the condenser viewed along the line X—X' in FIG. 2.

FIG. 3 shows a cross-sectional view of the level 14 of the condensate liquid at the opening 15 viewed along the X—X' in FIG. 2. Numeral 14a denotes a space surrounded with the level 14 of the condensate liquid and the upper inner wall of the conduit 13.

In FIG. 2, a vapor is withdrawn from the rectifying column for stripping hydrogen cyanide 2 at a point 2a and fed through line 9 from the inlet 20 for vapor to the heat exchange section 11 of the condenser 10 where a cooling medium such as industrial water and cooling water is introduced through line 11a and withdrawn through line 11b. The vapor is condensed with the cooling medium in the heat exchange section 11 and the condensate liquid is collected in the liquid reservoir section 12. On the other hand, non-condensing gas in the vapor is led to the outlet 23 for non-condensing gas from the opening 15 provided at the side wall 21 of the liquid reservoir section 12 through the upper space in the conduit 13 for withdrawing non-condensing gas, i.e. a region having, as an opening area, a space 14a surrounded with the level 14 of the condensate liquid and the upper inner wall of the conduit 13. If necessary or if desired, the non-condensing gas may be from the outlet 23 either simply returned to and withdrawn from the top of the extractive distillation or led to a device for recovering hydrogen cyanide or acrylonitrile. Also, an inhibitor for the polymerization of hydrogen cyanide such as acetic acid may be shed in the condenser 10. The condensate liquid is withdrawn from the outlet 24 of the condenser 10 and returned to the column 2 at a point 2b through line 19. With line 19 are provided a liquid transfer pump 22 and a liquid flow control valve 18. In this case, a liquid flow controller 17 regulates the liquid flow control valve 18 in such a manner as to maintain the flow amount at a liquid flow transmitter 16 constant.

In the process as set forth in FIG. 2, the condenser of this invention is employed for condensing a predetermined amount of vapor from the column 2. As one modification of this process, it is possible to conduct a so-called follow-up control by varying the set point value in accord with other process signals instead of maintaining the set point value at the liquid flow transmitter 16 constant. Further, the liquid flow control valve 18 can be manually regulated.

In the present process, the amount of condensation in the column 2 can be varied by varying the flow amount of condensate liquid returned to the column 2. For example, in order to increase the amount of condensation, the set point value at the liquid flow controller 17 is increased by the amount to be increased and the liquid flow controller 17 is operated in such a manner that the liquid flow control valve 18 is opened until the set point value becomes equal to the transmission value at the liquid flow transmitter 16. As a result, the amount of condensate liquid returned to the column 2 is increased and accordingly, the amount of the condensate liquid withdrawn from the condenser 10 is increased. Then the level 14 of the condensate liquid in the liquid reservoir section 12 of the condenser 10 is lowered and as a result, the space 14a in the conduit 13 for withdrawing non-condensing gas is increased with increased amounts of non-condensing gas withdrawn. Consequently, the pressure in the condenser 10 is reduced and the amount of the vapor withdrawn from the column 2 through line 9 is increased and becomes balanced with the amount of the condensate liquid withdrawn. In this case, the cooling capacity of the heat exchange section 11 is large enough to keep up with such an increase in the amount of the vapor. Finally, an equilibrium is established in the state where an increase in the amount of the vapor in accordance with the increase in the amount of the condensate liquid and a lowering of the level of the condensate liquid to some extent due to the increase in the amount of the non-condensating gas withdrawn are brought about. In order to decrease the amount of condensation in the column 2, the procedures opposite to those as described above are taken.

According to the condenser of this invention, the amount of condensation can be varied by varying the opening area 14a in the conduit 13 for withdrawing non-condensing gas and accordingly, the amount of the non-condensing gas withdrawn. Thus, the range of the opening area varied corresponds to that of the amount of condensation varied. In this sense, it is necessary to design the dimension and the shape of the opening 15 and the conduit 13 in accordance with their requirements. When the amount of condensation is large, their dimension and shape must be large. This, however, is a matter of designing. The cross-sections of the opening 15 and the conduit 13 for withdrawing non-condensing gas are not necessarily circular as are shown in FIGS. 2 and 3 and they can be of any shape such as oval, square, triangle and polygon, if necessary or if desired.

Furthermore, the condenser of this invention can be employed for a vapor withdrawn from a distillation column which not contain non-condensing gas. In such a case, a non-condensing gas such as air and nitrogen gas can be mixed with the vapor at an appropriate point of line 9 to achieving the same effect as with the vapor containing non-condensing gas.

According the condenser of this invention, the amount of condensation can be efficiently varied or stabilized by such a simple regulating process. Also, in using the condenser of this invention, the level of the condensate liquid is self-controlled and any control of the level of the condensate liquid is substantially unnecessary, contrary to the fact that according to a conventional condenser, the level of the condensate liquid has no self-controllability and that some control system is required. Furthermore, as in FIG. 2, insertion of an element for lowering or fluctuating pressure such as a valve into the line of the condensate liquid is sufficient and accordingly, it is unnecessary to take account of the pressure drop by the element in the condenser itself, i.e. caused by the difference in temperature between the vapor and the cooling water in the heat exchange section of the condenser.

The following Examples are given to illustrate the present invention more specifically. However, it should be understood that the invention is in no way limited by these Examples. All parts and percentages in these Examples are by weight unless otherwise indicated.

EXAMPLE 1

To the 21st plate from the bottom of a rectifying column for stripping hydrogen cyanide having 32 plates as set forth in FIG. 1 was fed a liquid containing 85% of acrylonitrile, 10% of hydrogen cyanide, 5% of water and traces of other organic compounds at 40° C. at a flow rate of 1.2 metric ton per ton of acrylonitrile and then 70% of an ascending vapor in the column was continuously withdrawn at the 26th plate from the bottom of the column and condensed by cooling with cooling water of 30° C. in a condenser. Non-condensing gas was continuously withdrawn from the condenser while the condensate liquid containing 17.2% of acrylonitrile, 78.2% of hydrogen cyanide and 4.6% of water was returned to the 25th plate from the bottom of the column at a flow rate of 0.60 metric ton per metric ton of acrylonitrile. The rectification was conducted under the following conditions;

Pressure of Top of Column: 0.1 Kg/cm$^2$G
Temperature of Top of Column: 30° C.
Temperature of 26th Plate: 48.6° C.

As a result, in this operation the heat load at the overhead condenser was reduced by 80% compared with the conventional operation, and the concentration of acrylonitrile in the hydrogen cyanide from the top of the column was 2,900 ppm by volume and that of hydrogen cyanide in the acrylonitrile and water withdrawn from the bottom of the column was 30 ppm without undergoing any deterioration in their purities.

EXAMPLE 2

To the 27th plate from the bottom of a rectifying column for stripping hydrogen cyanide and dehydration having 45 plates was fed a liquid containing 85% of acrylonitrile, 10% of hydrogen cyanide, 5% of water and traces of other organic compounds at 40° C. at a flow rate of 1.2 metric ton per ton of acrylonitrile, and then 69% of an ascending vapor in the column was continuously withdrawn at the 35th plate from the bottom of the column and condensed by cooling with cooling water of 30° C. in a condenser. Non-condensing gas was continuously withdrawn from the condenser while the condensate liquid containing 29.4% of acrylonitrile, 64.3% of hydrogen cyanide and 6.3% of water was returned to the 34th plate from the bottom of the column at a flow rate of 0.59 metric ton per metric ton of acrylonitrile. All of the liquid descending was withdrawn from the column at the 15th plate from the bottom of the column, cooled to 40° C. and separated into two phases, i.e. an organic phase and an aqueous phase in a decanter. Then the organic phase was returned to the column at the 14th plate from the bottom of the column while the aqueous phase was removed from the decanter.

The rectification was conducted under the following conditions;

Pressure of Top of Column: 0.1 Kg/cm$^2$G
Temperature of Top of Column: 30° C.
Temperature of 35th Plate: 55° C.

As a result, in this operation the heat load at the overhead condenser was reduced by 81% compared with the conventional operation, and the concentration of acrylonitrile in the hydrogen cyanide from the top of the column was 3,000 ppm by volume and that of hydrogen cyanide in the acrylonitrile and water withdrawn from the bottom of the column was 30 ppm without undergoing any deterioration in their purities.

What is claimed is:

1. A process for purifying a crude olefinically unsaturated nitrile containing hydrogen cyanide and water by feeding the crude olefinically unsaturated nitrile at a point above the middle of a rectifying column for stripping hydrogen cyanide, withdrawing and condensing a vapor of hydrogen cyanide from the top of the column while withdrawing the olefinically unsaturated nitrile and water from the bottom of the column, which process comprises withdrawing a vapor in the column at a point between the top of the column and the point of introduction of the crude olefinically unsaturated nitrile, at a substantially constant rate and wherein the temperature is about 40° C. to about 75° C. cooling and condensing the vapor withdrawn in a condenser having an outlet for non-condensing gas while continuously withdrawing non-condensing gas in the vapor from the condenser, and returning the condensate liquid to the column at an intermediate point between the point of introduction of the crude olefinically unsaturated nitrile and the top of the column.

2. The process of claim 1, wherein the crude olefinically unsaturated nitrile is a crude acrylonitrile.

3. The process of claim 2, wherein the crude acrylonitrile contains about 60 to about 90% by weight of acrylonitrile, about 5 to about 15% by weight of hydrogen cyanide, about 3 to 10% by weight of water and a small amount of carbonyl compounds.

4. The process of claim 1, wherein the withdrawal of the vapor in the column is conducted at a point where the temperature in the column is about 55° C. to about 70° C.

5. The process of claim 1, wherein the condensate liquid in the condenser is returned to the column at a point where the temperature in the column is about 40° C. to about 75° C.

6. The process of claim 1, wherein the condensate liquid in the condenser is returned to the column at a point just below the point of withdrawal of the vapor.

7. The process of claim 1, wherein the condensate liquid in the condenser is returned to the column at the same point as the point of withdrawal of the vapor.

8. The process of claim 1, wherein the amount of vapor for the withdrawal ranges from about 50 to about 90% by weight of the total amount of the ascending vapor in the column.

9. The process of claim 1 which additionally comprises withdrawing from the column at an intermediate point between the point of introduction of the crude olefinically unsaturated nitrile and the bottom of the column substantially all of the liquid descending in the column, cooling and separating the liquid withdrawn into an organic phase and an aqueous phase, and returning the organic phase to the column at a point below the intermediate point while withdrawing the aqueous phase.

10. The process of claim 9, wherein the amount of the vapor for the withdrawal ranges from about 50 to about 90% by weight of the total amount of the asending vapor in the column.

11. The process of claim 9, wherein the condensate liquid in the condenser is returned to the column at a point where the temperature in the column is about 40° C. to about 75° C.

* * * * *